(12) United States Patent
Lin et al.

(10) Patent No.: US 6,511,660 B1
(45) Date of Patent: Jan. 28, 2003

(54) OPHTHALMIC DRUG DELIVERY FORMULATIONS AND METHOD FOR PREPARING THE SAME

(76) Inventors: Hong-Ru Lin, 9F-1, No. 87, Sec. 2 Fa-Tung Road, Tainan (TW), 701; Kuo-Chun Sung, No. 20, An-E Road, Keelung (TW)

( * ) Notice: Subject to any disclaimer, the term of this patent is extended or adjusted under 35 U.S.C. 154(b) by 73 days.

(21) Appl. No.: 09/725,006

(22) Filed: Nov. 29, 2000

(30) Foreign Application Priority Data

Dec. 15, 1999 (TW) ........................................ 88122319 A (51) Int. Cl.[7] .............................................. A61K 31/74
(52) U.S. Cl. .................... 424/78.04; 514/912; 514/913
(58) Field of Search ...................... 424/78.04; 514/912, 514/913

(56) References Cited

U.S. PATENT DOCUMENTS

| | | |
|---|---|---|
| 4,271,143 A | 6/1981 | Schoenwald et al. |
| 4,425,344 A | 1/1984 | Horlington |
| 4,425,345 A | 1/1984 | Horlington et al. |
| 4,868,287 A | 9/1989 | Sikes et al. |
| 4,888,168 A | 12/1989 | Potts et al. |
| 5,177,105 A | 1/1993 | Moll et al. |
| 5,252,318 A | 10/1993 | Joshi et al. |
| 5,427,778 A | 6/1995 | Finkenaur et al. |
| 5,593,683 A | 1/1997 | Viegas et al. |
| 5,639,469 A | 6/1997 | Benes et al. |
| 5,908,637 A | 6/1999 | Benes et al. |

*Primary Examiner*—Zohreh Fay
(74) *Attorney, Agent, or Firm*—Fei-Fei Chao; Venable, Baetjer, Howard & Civiletti, LLP (57) ABSTRACT

The present invention provides novel ophthalmic drug delivery formulation which comprises a mixture of Carbopol and Pluronic. Carbopol is a trademark of B.F. Goodrich Company's high molecular weight carboxy vinyl polymers (MW above 1,000,000). Pluronic belongs to a class of block copolymers containing polyoxyethylene and polyoxypropylene. The preferred weight percentages of Carbopol and Pluronic in the ophthalmic drug delivery formulation are 0.3% of Carbopol and 14% of Pluronic. The ocular bioavailability is greatly enhanced by the use of the ophthalmic drug delivery formulation of the present invention.

15 Claims, 5 Drawing Sheets

OPHTHALMIC DRUG DELIVERY FORMULATIONS AND METHOD FOR PREPARING THE SAME

RELATED APPLICATION

The present invention claims the priority of Taiwan patent application serial No. 88122319, filed on Dec. 15, 1999, which is herein incorporated by reference.

FIELD OF THE INVENTION

The present invention relates to novel ophthalmic drug delivery formulations which comprise, without limitation, a Carbopol solution, a Pluronic solution, or a combination of Carbopol and Pluronic. This formulation is a free flowing liquid with low viscosity at non-physiological condition and undergoes in situ phase transition to form strong gel at physiological condition. The ophthalmic drug delivery formulations are especially suitable for use with ophthalmic drugs such as pilocarpine hydrochloride to treat glaucoma. The present invention also relates to the method for making the ophthalmic drug delivery formulation.

BACKGROUND OF THE INVENTION

Most of the conventional ophthalmic drug delivery systems encounter great problems due to unique physiological conditions of the eye, i.e., when a conventional liquid ophthalmic formulation is applied to the eye, upon instillation, it is immediately eliminated from the precorneal area of the eye because of lacrimal secretion and nasolacrimal drainage. As a result, only 1–10% of the ophthalmic drugs can be utilized by patients and a frequent instillation of concentrated solutions is necessary in order to achieve the desired therapeutic effects.

To lengthen the retention time of instilled ophthalmic drug in the eye and to enhance the bioavailability of the ophthalmic drug, various ophthalmic vehicles have been developed. Examples of such ophthalmic vehicles include various inserts, ointments, suspension, and aqueous gels. However, these ophthalmic vehicles have their drawbacks. For example, the use of ointments often causes blurred vision. Also, insert is not particularly popular among patients due to its low patient compliance.

Among the ophthalmic vehicles, one kind, the so-called in situ gel forming systems, has been particularly useful for prolonging precorneal retention time and improving ocular bioavailability of the ophthalmic drugs. Typically, an in situ gel forming system is made of polymers. These polymers can undergo a phase transition from a solution (liquid) to a gel once they have been instilled in the cul-de-sac of the eye.

Various in situ gel forming systems have been reported. For example, Gurny et al., *J. Contr. Release* (1985), 2:353–361, discloses an ocular drug delivery system which includes cellulose acetophthalate (CAP) latex and Carbopol solution. Carbopol is the trademark of B.F. Goodrich Company's carboxy vinyl polymers. Rozier et al., *Int. J. Pharm.* (1989), 57: 163–168, discloses an ion-activated gelling vehicle with a trademark of Gelrite®. However, Rozier et al.'s gelling vehicle has the disadvantages of being converted into gel in the presence of mono- or divalent cations.

Joshi et al.'s U.S. Pat. No. 5,252,318 discloses reversibly gelling aqueous compositions which contain at least one pH-sensitive reversibly gelling polymer (such as carboxy vinyl linear or branched or cross-linked polymers of the monomers) and at least one temperature-sensitive reversibly gelling polymer (such as alkylcellulose, hydroxyalkyl cellulose, block copolymers of polyoxyethylene and polyoxypropylene, and tetrafunctional block polymers of polyoxyethylene and polyoxypropylene and ethylenediamine). Joshi et al.'s compositions exhibit significant changes in viscosity in response to substantially simultaneous changes in both temperature and pH.

Kumar et al., *J. Ocular Pharmacol.* (1994), 10: 47–56, discloses an ocular drug delivery system based on a combination of Carbopol and methylcellulose. The sol-gel transition of the combination occurs primarily due to an increase in pH because of the presence of Carbopol. Kumar et al., *J. Pharm. Sci.* (1995), 84: 344–348 (1995), discloses yet another ocular drug delivery system containing Carbopol and hydroxyproplymethylcellulose. In both systems, a viscosity-enhancing polymer is added to achieve a reduction in Carbopol concentration without compromising the in situ gelling properties as well as overall rheological behaviors.

Finkenaur et al.'s U.S. Pat. No. 5,427,778 discloses a gel formulations contains a polypeptide growth factor and a water soluble, pharmaceutically or ophthalmically compatible polymeric material for providing viscosity within various ranges determined by the application of the gel. Both Carbopol gels and Pluronic gels, respectively, are disclosed in the patent. Pluronic is the trademark for BASF's polyoxyethylene-polyoxypropylene block copolymers.

Viegas et al.'s U.S. Pat. No. 5,593,683 discloses a method for making a thermoreversible gels for drug or diagnostic agent delivery. The gels contain a pharmaceutical agent, a surfactant, and a polyalkylene polyether. The combined total amount of the surfactant and the polyalkylene polyether does not exceed about 10% by weight.

Because most of the in situ gel forming systems described above require the use of high concentrations of polymer to form gel upon instillation in the eye, they are not suitable for use in ophthalmic drug delivery. Also, in the case of Carbopol polymer, the increase in Carbopol concentration produces an acidic environment which may in turn cause irritation to the eye tissue. Thus, finding a gelling vehicle which demonstrates good solubility and fluidity at non-physiological condition (i.e., pH 4.0 at 25° C.), and can be converted to gel at physiological condition (i.e., pH 7.4, 37° C.) is definitely in demand particularly in the ophthalmic drug delivery industry.

SUMMARY OF THE INVENTION

The present invention provides ophthalmic drug delivery formulations which either contain Carbopol® (hereinafter "Carbopol") or Pluronic® (hereinafter "Pluronic") or a combination of Carbopol and Pluronic. The preferred formulation is the one containing a combination of Carbopol and Pluronic.

Carbopol is a trademark of B.F. Goodrich Company. It contains a group of carboxy vinyl polymer (or polyacrylic acid polymer). The preferred carboxy vinyl polymer is a high molecular weight (preferably MW above 1,000,000; and most favorably MW above 3,000,000) polymer, such as Carbopol 934P which has a molecular weight of about 3,000,000. The preferred Carbopol concentration is 0.3–0.4% (w/v), most favorably 0.3% (w/v).

Pluronic is a trademark of BASF's polyoxyethylene-polyoxypropylene block copolymers. The preferred Pluronic is Pluronic F-127. The preferred concentration of Pluronic is 14% (w/v).

In the ophthalmic drug delivery formulation containing a combination of Carbopol and Pluronic, the preferred concentration of Carbopol is no more than 0.5% (w/v), most favorably 0.3%. The preferred Pluronic concentration is no more than 15% (w/v), most favorably 14% (w/v).

The ophthalmic drug delivery formulation of the present invention has the characteristics of being in free flowing state at non-physiological condition (i.e., pH 4.0 and 25° C.) and forming gel at physiological condition (i.e., pH 7.4 and 37° C.).

The ophthalmic drug delivery formulation of the present invention is especially suitable for use with any of the ophthalmically active drugs, particularly amine drugs known for use in the treatment of diseases of the eye, such as glaucoma. The preferred drug is pilocarpine hydrochloride.

The present invention also provides a method for preparing the ophthalmic drug delivery formulation containing a combination of Carbopol and Pluronic, which includes the following steps: (1) dispersing the Carbopol in water to form a Carbopol solution (preferably at 0.3% [w/v]); and (2) adding the preferred amount of Pluronic (preferably at 14% [w/v]) in the Carbopol solution to form said ophthalmic drug delivery formulation. Additionally, an ophthalmic drug, such as pilocarpine hydrochloride can be added to the ophthalmic drug delivery formulation.

Finally, the present invention provides a method of treating patients with eye diseases, such as glaucoma, by topically administering to the patient an effective amount of the ophthalmic drug delivery system containing 0.3% (w/v) of Carbopol and 14% (w/v) of Pluronic. The preferred ophthalmic drug is pilocarpine hydrochloride. The preferred pH of the ophthalmic drug delivery system is no more than pH 5.5.

DETAILED DESCRIPTION OF THE INVENTION

An ideal ophthalmic in situ gelling delivery system should be a free flowing liquid with low viscosity at non-physiological condition (pH 4.0 and 25° C.) to allow reproducible administration into the eye as drops. It should also undergo in situ phase transition to form strong gel capable of withstanding shear forces in the cul-de-sac of the eyes and sustain drug release at physiological condition (pH 7.4 and 37° C.).

The present invention provides in situ gel forming formulations which comprise (1) a Carbopol solution; (2) a Pluronic solution, and (3) a combination of Carbopol and Pluronic solutions.

Carbopol is the trademark of B. F. Goodrich Company's carboxy vinyl polymers, which generally are high molecular weight ("MW") polymers (MW above 1,000,000). Specifically, Carbopol 934P has a MW of about 3,000,000 and Carbopol 940 is about 4,000,000. The preferred Carbopol is Carbopol 934P. The preferred Carbopol concentration is 0.3–0.4% (w/v). That is because when Carbopol was dissolved in distilled and deionized water, the solution displayed similar rheological behavior (i.e., free flowing property) in the 0.3–0.4% concentration range.

However, when the concentration of the Carbopol solution decreased to equal to or less than 0.2% (w/v), although its free flowing properties at non-physiological conditions (e.g., pH 4.0 and 25° C.) remained the same, it lost the property to form strong gel at physiological condition (e.g., pH 7.4 and 37° C.).

On the other hand, when the concentration of the Carbopol solution increased to equal to or greater than 0.5% (w/v), the solution formed stiff gel even at pH 4.0 and 25° C. due to high viscosity. Also, as the concentration of the Carbopol solution increased, the solution became highly acidic and it would not be easy to be neutralized by the buffering capability of the natural tear fluid. As a result, the addition of the Carbopol solution with a concentration over 0.5% (w/v) might irritate the eyes and cause damage to the eye tissues.

Only when the concentration of the Carbopol solution was at a range between 0.3–0.4% (w/v), the free flowing properties (i.e., at liquid state) at non-physiological condition and gelling properties at physiological condition were achieved. Accordingly, the optimum concentration of Carbopol for use in the in situ gel forming agent was 0.3–0.4% (w/v), preferably at 0.3% (w/v).

Pluronic is the trademark for BASF Corporation's (Parsippany, N.J.) polyoxyethylene-polyoxypropylene block copolymer. Pluronic exhibits reverse thermal gelation behavior, and has good drug release characteristics as well as low toxicity. However, low molecular weight Pluronic polyols do not form gels at any concentration in water. Pluronic F-68 forms a gel at a minimum concentration of 50–60% at room temperature. Pluronic F-108 forms a gel at 30% concentration. Pluronic F-127 (also known as Poloxamer 407) forms a gel at 20% concentration in water at 25° C. The preferred Pluronic used in the present invention is Pluronic F-127, which has the formula of: H[OCH$_2$CH$_2$]$_{49}$[OCHCH$_2$]$_{67}$[OCH$_2$CH$_2$]$_{49}$OH.

When the concentration of the Pluronic solution was equal to or less than 13% (w/v), the solution was at a free flowing property (i.e., liquid state) in both non-physiological and physiological conditions. As the Pluronic concentration increased to equal to or greater than 15% (w/v), the solution became stiff gel at non-physiological condition. Thus, the optimum concentration for Pluronic solution to be used as an in situ gel forming system was 14% (w/v).

The preferred concentrations for the formulation containing a combination of Carbopol and Pluronic were 0.3% (w/v) of Carbopol and 14% (w/v) of Pluronic. With these concentrations, the formulation could flow freely at non-physiological condition and convert into gel in physiological condition. In addition, the rheological properties of the formulation were not affected by the incorporation of drug.

Based on the in vitro and in vivo results described in the Examples Section (infra), the formulation containing the combined Carbopol and Pluronic performed better, particularly in retaining drugs, than the individual formulations.

The above mentioned ophthalmic drug delivery formulations are adaptable for use with any of the ophthalmically active drugs, particularly amine drugs known for use in the treatment of diseases of the eye. These ophthalmic drugs include pilocarpine, epinephrine, tetracycline, phenylephrine, eserine, phospholine iodide, demecarium bromide, cyclopentolate, homatropine, scopolamine, chlortetracycline, bacitracin, neomycin, polymixin, gramicidin, oxytetracycline, chloramphenicol, gentamycin, penicillin, erythromycin, carbachol, sulfacetamide, polymixin B, idoxuridine, isoflorophate, fluoromethalone, dexamethasone, hydrocortisone, hydrocortisone acetate, 21-phosphate, fluorocinolone, medrysone, prednisolone, methyl prednisolone, prednisolone 21-phosphate, prednisolone acetate, betamethasone and triamcinolone. The preferred ophthalmic drug is pilocarpine hydrochloride.

The following examples are illustrative, but not limiting the scope of the present invention. Reasonable variations, such as those occur to reasonable artisan, can be made herein without departing from the scope of the present invention.

EXAMPLE 1

Preparation of Ophthalmic Drug Delivery Formulations

Materials

Carbopol (934P NF, B.F. Goodrich), Pluronic (F-127, BASF), pilocarpine hydrochloride (Sigma) were used as received. All other chemicals, including sodium chloride, sodium hydrogen carbonate, calcium chloride dihydrate and sodium hydroxide pellets were purchased from Merck and were used as received.

Sample Preparation

The Carbopol solutions (0.1 to 0.6% [w/v], 1.0 and 2.0% [w/v]) were prepared by dispersing the required amount in distilled, deionized water with continuous stirring until completely dissolved.

The Pluronic solutions (10 to 25% (w/v)) were prepared by dispersing the required amount of polymer in distilled, deionized water with continuous stirring for 1 hour. The partially dissolve Pluronic solutions were stored in the refrigerator until the entire polymer was completely dissolved (approximately 24 hours).

The Carbopol/Pluronic solutions were prepared by dispersing the required amount of Pluronic in the desired concentration of Carbopol with continuous stirring for 1 hour. The partially dissolved solutions were then refrigerated until solutions were thoroughly mixed (approximately 24 hours). The reported composition of Carbopol/Pluronic mixture was the final concentration of Carbopol and Pluronic content in the mixture.

The pilocarpine-containing polymer solutions were prepared by adding the desired amounts of pilocarpine to the Carbopol, Pluronic, or Carbopol/Pluronic solutions with continuous stirring until thoroughly mixed.

All the sample solutions were adjusted to pH 4.0±0.1 or 7.4±0.1 by 0.5 M sodium hydroxide solution and then stored in the refrigerator prior to the evaluation of their rheological properties.

Results

From the sample preparation procedures, it was observed that the Carbopol solutions with concentrations equal to or less than 0.2% (w/v) had free flowing properties at non-physiological condition. However, these compositions could not form strong gel at physiological condition. On the other hand, when the Carbopol concentrations equal to or greater than 0.5% (w/v), stiff gels were formed even though the pH was at 4.0 and the temperature was at 25° C. It was found that the Carbopol solution at 0.3–0.4% (w/v) remained at liquid state at pH 4.0 and 25° C. and gelled upon exposure to physiological conditions. It was also found that the Carbopol solution at 0.3–0.4% (w/v) concentration range had similar rheological behavior.

From the preparation procedures of the Pluronic solutions, it was found that for the Pluronic concentrations equal to or less than 13% (w/v), the solution exhibited at sol (liquid) state in both non-physiological and physiological conditions. As the Pluronic concentrations equal to or greater than 15% (w/v), the solution already became stiff gel at non-physiological condition. These observations indicated that the optimum concentration for the Pluronic solution should be 14% (w/v).

EXAMPLE 2

Rheological Studies

Experimental Design

The rheological studies were carried out on a cone (4°) and plate geometry viscometer (Brookfield RVCP DV-III). The viscosity and shear stress of the sample solutions were measured at various shear rates at 25° C. and 37° C., respectively. The temperature was maintained within ±0.1° C. by a recirculating bath (Wisdom) connected to the sample cup of viscometer. The samples were equilibrated on the plate for 5 minutes to reach the running temperature prior to each measurement. A typical run comprised of changing the shear rate from 0 to 200 s$^{-1}$ at a controlled ramp speed, a 0.1-min wait at 200 s$^{-1}$, and finally a decrease in shear rate to 0 s$^{-1}$ at the same controlled ramp speed.

Results (a) Rheological Behaviors of Ophthalmic Drug Delivery Formulations without Pilocarpine The rheological behaviors of various polymer solutions were investigated as a function of temperature and pH. All measurements were performed in triplicate with good reproducibility and the standard deviations were all within 3%.

Figure 1:
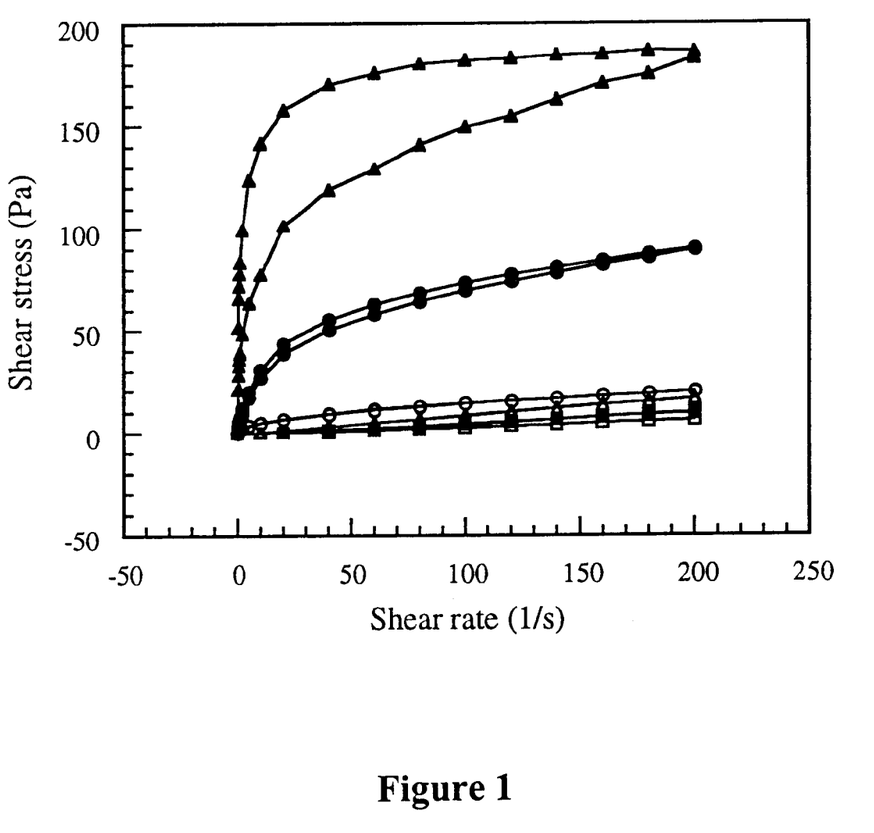
FIG. 1 shows the shear stress versus shear rate flow curves of different aqueous polymer solutions. (○) shows 0.3% Carbopol solution measured at pH 4.0 and 25° C.; (●) shows 0.3% Carbopol solution measured at pH 7.4 and 37° C.; (□) shows 14% Pluronic solution measured at pH 4.0° and 25° C.; (■) shows 14% Pluronic solution measured at pH 7.4 and 37° C.; (Δ) shows 0.3% Carbopol/14% Pluronic solution measured at pH 4.0 and 25° C.; (▲) shows 0.3% Carbopol/14% Pluronic solution measured at pH 7.4 and 37° C. All the measurements were performed in triplicate and the standard deviations were all within 3%.

FIG. 1 shows the shear stress versus shear rate flow curves of the Carbopol solution (0.3% (w/w)), Pluronic solution (14% (w/w)) as well as the mixture of Carbopol (0.3%(w/w))/Pluronic (14% (w/w)) solution at non-physiological and physiological conditions. For the Carbopol solution at physiological condition, the medium resisted the initial rotary motion and a sudden increase in the shear stress was observed at higher shear rate. The solution began to flow after the shear stress reached its yield point. Accordingly, the flow curve for the Carbopol solution at physiological conditions demonstrated a pseudoplastic behavior.

FIG. 1 also shows that, for the Carbopol solution at non-physiological conditions as well as for the Pluronic solution at either non-physiological or physiological conditions, the shear stress increased linearly with an increase in shear rate, demonstrating a Newtonian flow behavior. Despite the flow curve of the Carbopol/Pluronic solution at pH 4.0 and 25° C. which shows a Newtonian flow behavior, nevertheless, a pseudoplastic flow behavior with a hysteresis was observed for the Carbopol/Pluronic solution at pH 7.4 and 37° C.

For all of the polymer systems studied, the shear stresses at pH 7.4 and 37° C. were higher than those at pH 4.0 and 25° C. For instance, at shear rate of 100 $s^{-1}$, the shear stresses of the Carbopol and Carbopol/Pluronic solutions at physiological condition were approximately 5 and 18 times greater than those at non-physiological condition, respectively, suggesting the occurrence of phase transition between these two conditions for both systems. Only slightly higher shear stresses were observed for the Pluronic solutions at physiological condition comparing to those at non-physiological condition for the shear rates ranging from 0 to 200 $s^{-1}$. The observed phase transition for the Carbopol solution was mediated by the increase in pH value from 4.0 to 7.4, which could be attributed to ionization of the Carbopol polymer. At pH 7.4, the mutual repulsion of the ionized carboxyl groups might produce more stretched the Carbopol backbone and those carboxyl groups might also form stable hydrogen bonds with water molecules through hydrophilic interactions. On the other hand, the hydrophobic nature of the Carbopol backbone might form hydrophobic interchain aggregation; this cross-linking phenomenon might result in the formation of more viscous gel at pH 7.4 environment.

The increase in shear stress for the Pluronic solution from non-physiological to physiological conditions was mediated by temperature and could be explained by the structure characteristics of Pluronic. Pluronic is a class of block copolymers, consisting of poly(oxyethylene) and poly(oxypropylene) units, with the general formula poly(oxyethylene)$_x$-poly(propylene)$_y$-poly(oxyethylene)$_x$. Poly(oxyethylene) (PEO) is predominantly hydrophilic whereas poly(oxypropylene) (PPO) is hydrophilic at low temperatures and becomes more hydrophobic at higher temperatures. Once blocks of PEO and PPO are combined, one can expect amphiphilic characteristics and aggregation phenomena at higher temperature. That is, when the polymer concentration and the characteristic temperature are above a critical point, this triblock copolymer forms micelles. The formation of micelles may increase the viscosity of the delivery system and thus lead to the sol-gel transition at higher temperature.

The slight increase in shear stress as the environment of the Pluronic solution changed from non-physiological condition to physiological condition can be attributed to the lower Pluronic concentration used in the present study in order to keep free flowing properties at non-physiological condition, particularly since previous publication have shown that over 24% (w/w) of Pluronic concentration (Hvidt et al., *J. Phys. Chem.* (1994), 98:12320–12328) is need to observe significant sol-gel phase transition.

Although the shear stress of the Carbopol solution increased significantly at physiological condition, a stronger gel could be formed by combining the Pluronic with the Carbopol solutions. FIG. 1 shows that, at pH 4.0 and 25° C., the shear stress of the Carbopol/Pluronic solution was higher than that of the Pluronic solution and slightly lower than that of the Carbopol solution at each shear rate. However, at pH 7.4 and 37° C., the shear stress of the Carbopol/Pluronic solution was significantly greater than that of the Carbopol or Pluronic solution, respectively, at each shear rate. This observation can be explained by the formation of crosslinks between the two polymers: the water molecules act as crosslinking agent to form hydrogen bonds between the carboxyl groups of Carbopol and ether groups of Pluronic, which lead to the formation of a three-dimensional network and stronger gel. Accordingly, at physiological condition, the ionic repulsion between the negatively charged carboxyl groups may produce more stretched Carbopol structure and thus form increased hydrogen bonds with the exposed PEO structure, which may subsequently result in the significantly increased in shear stress response and the phase transition phenomenon.

The above results and inferences clear indicate that the gel strength of the polymer solution in the physiological condition can be enhanced significantly by combining the two individual solutions. Since, from the observation of the sample preparation, an ophthalmic solution containing 0.3% (w/v) of Carbopol and 14% (w/v) of Pluronic could flow freely at non-physiological condition and form gel at physiological condition. Thus, without increasing the concentration of individual polymer solution, this mixed polymer solution should be able to administer into the eye as drops and form stronger gel following the phase transition.

The above results also suggest that the combined use of Carbopol and Pluronic may provide more strength to withstand the low shear forces likely to encountered in the cul-de-sac of the eye as well as prolong the retention time of the drug in the eye.

All of the flow curves shown in FIG. 1 were investigated by varying the shear rate from 0 to 200 $s^{-1}$ at a controlled ramp speed, a 0.1-min wait at 200 $s^{-1}$, and finally a decrease in shear rate to 0 $s^{-1}$ at the same controlled ramp speed. Except for the 0.3% Carbopol/14% Pluronic solution, most of the ophthalmic drug delivery systems showed pseudoplastic or Newtonian flow behavior with no hysteresis. The hysteresis phenomenon observed in the flow curve of 0.3% Carbopol/14% Pluronic solution at pH 7.4 and 37° C. may be due to the structural changes in the gel following the exposure to shear forces.

As mentioned above, when mixing the triblock copolymer (Pluronic) with Carbopol solution at physiological condition, the combined solution forms a network structure via hydrogen bonds. This polymer network can be characterized as a viscoelastic material. The viscoelastic material normally shows hysteresis phenomenon under cyclic deformation.

Figure 2:
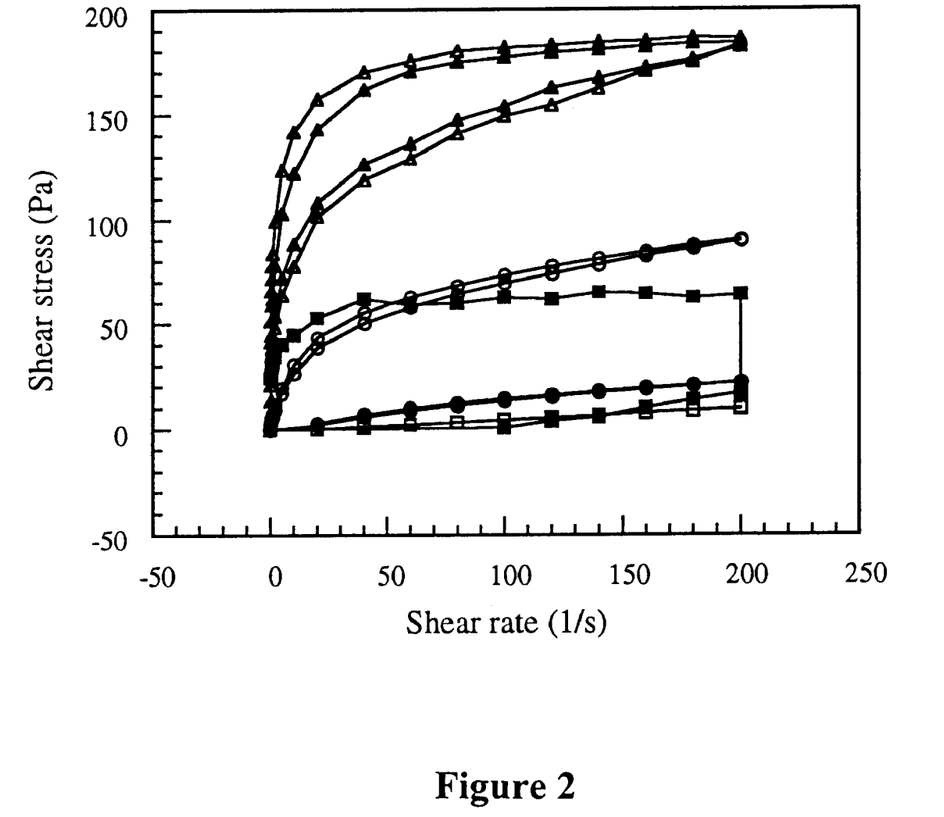
FIG. 2 shows the effect of drug on the shear stress versus shear rate flow curves of different aqueous polymer solutions at pH 7.4 and 37° C. (○) shows 0.3% Carbopol solution; (●) shows pilocarpine-containing 0.3% Carbopol solution; (□) shows 14% Pluronic solution; (■) shows pilocarpine-containing 14% Pluronic solution; (Δ) shows 0.3% Carbopol/14% Pluronic solution; (▲) shows pilocarpine-containing 0.3% Carbopol/14% Pluronic solution. All the measurement were performed in triplicate and the standard deviations were all within 0.3%.

(b) Rheological Behaviors of Ophthalmic Drug Delivery Formulations with Pilocarpine In order to investigate the effects of pilocarpine hydrochloride on the rheological behaviors of the ophthalmic drug delivery formulations, the rheological studies on the pilocarpine-containing polymer solution at pH 7.4 and 37° C. were performed and the results are shown in FIG. 2. To the 0.3% Carbopol solution, the incorporation of pilocarpine did not change the pseudoplastic flow behaviors. However, the shear stresses of the drug-containing Carbopol solution were much lower than those of the Carbopol solution alone.

The results may be explained by the interactions between pilocarpine and Carbopol polymer. When pilocarpine was added into the Carbopol solution at physiological condition, the positively charged amine group in pilocarpine may react with the negatively charged carboxyl group in Carbopol. These electrostatic interactions may disrupt the stability of the hydrogen bonds. In addition, pilocarpine may act as a plasticizer to mask the hydrophobic interactions between the backbone chains of Carbopol through selectively solvating the polymer chains.

For the pilocarpine-containing 14% Pluronic solution, a Newtonian flow behavior was observed and this flow behavior was similar to that of Pluronic solution. The shear stresses of pilocarpine-containing Pluronic solution measured from 0 to 200 $s^{-1}$ were close to those of the Pluronic solution, suggesting no significant interference between pilocarpine and Pluronic polymer. However, the hysteresis phenomenon was very pronounced for the pilocarpine-containing Pluronic solution, the reason behind this is unclear and needs further study.

These results show that the shear stress of the Carbopol or the Pluronic solution, respectively, was affected by the incorporation of drug into the solution. In other words, the viscosity of the individual polymer solution as well as the ability of the individual polymer solution to withstand the shear forces in the cul-de-sac were affected.

However, this untoward effect was minimized when the combination of Carbopol and Pluronic was used. As shown in FIG. 2, the 0.3% Carbopol/14% Pluronic solution with pilocarpine had similar flow behavior as the 0.3% Carbopol/14% Pluronic solution without pilocarpine, suggesting that the incorporation of pilocarpine did not disrupt the strong three-dimensional gel network formed at physiological condition.

Figure 3:
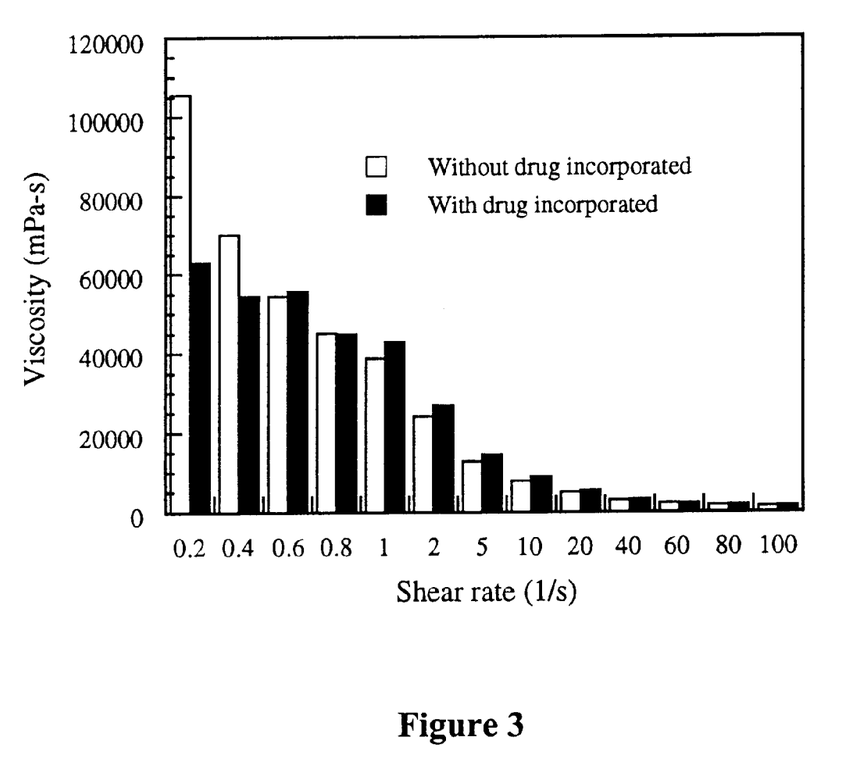
FIG. 3 shows the comparison of viscosity between (□) 0.3% Carbopol/14% Pluronic solution and (■) pilocarpine-containing 0.3% Carbopol/14% Pluronic solution at different shear rates measured at pH 7.4 and 37° C.

In fact, as shown in FIG. 3, except for the shear rate at 0.2 $s^{-1}$, similar viscosities were also observed between the Carbopol/Pluronic solution with pilocarpine and Carbopol/Pluronic solution without pilocarpine at physiological conditions, confirming that the rheological behavior of the Carbopol/Pluronic solution was not significantly affected by the incorporation of pilocarpine hydrochloride.

EXAMPLE 3

In Vitro Release Studies

Experimental Design

The in vitro drug release from various polymer solutions was first carried out by filling 3 g of pilocarpine-containing polymer solution into small, circular plastic containers (2.5 cm i.d. and 1.5 cm i.d.) in triplicate and placing each container in a 1000-mL beaker. Care was taken to make sure that no air bubbles were inside the polymer solutions. The beaker was then filled with 1000 ml of simulated tear fluid ("STF") (containing 0.67 g of NaCl, 0.20 g of $NaHCO_3$, 0.008 g of $CaCl_2.2H_2O$, and distilled, deionized water to 100 g) and place in a circulating water bath equipped with stirring rods to stir the release medium. The temperature and stirring rate were maintained at 37° C. and 75 rpm, respectively. Aliquots (1 mL each time) were withdrawn from the release mediums at each sampling time. The samples were filtered through 0.45-mm syringe filters and subjected to HPLC analysis to determine the pilocarpine concentrations.

The HPLC chromatographic system consisted of a pump (Hitachi L-7100), and autosampler (Hitachi L-7200), an UV detector (Hitachi L-7420), and an integrator (Hitachi D-2500). A normal phase silica column ($\mu$ Porasil, 3.9 mm×300 mm, 10 $\mu$m, Waters) was utilized for drug separation, while an acetonitrile-pH 3.5 acetate buffer system (80:20) was used as the mobile phase. The flow rate and UV wavelength were 0.9 mL/min and 220 nm, respectively. The injection volume was 100 $\mu$l. The drug concentrations were determined by measuring the peak area and comparing with the peak area of known standards.

Results

Figure 4:
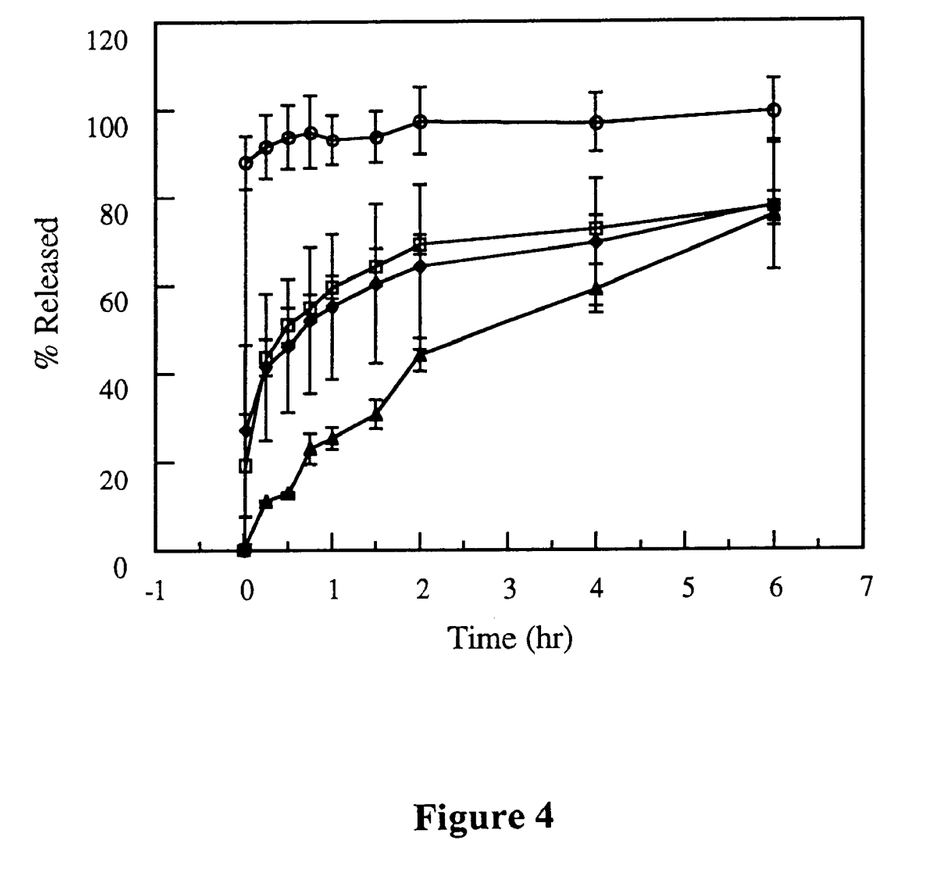
FIG. 4 shows the cumulative amount of pilocarpine released as a function of time from various pilocarpine-containing solutions. (□) shows pilocarpine-containing 0.3% Carbopol solution, (♦) shows pilocarpine-containing 14% Pluronic solution, (▲) shows pilocarpine-containing 0.3% Carbopol/14% Pluronic solution, and (○) shows pilocarpine-containing STF (simulated tear fluid).

FIG. 4 shows the cumulative amount of pilocarpine released versus time profiles for various drug-containing polymer solutions and the drug-containing STF (simulated tear fluid). All the polymer solutions and the STF contained 0.1% (w/w) pilocarpine hydrochloride. For the drug-containing STF, almost all of the pilocarpine released immediately after the start of release experiment. In the case of pilocarpine-containing 0.3% Carbopol solution, the drug released about 19% to the medium after one minute and then the drug gradually released afterwards. Approximately 78% of the pilocarpine released from the Carbopol solution after 6 hours. The pilocarpine-containing Pluronic solution had similar release trend as the Carbopol solution, which may be attributed to the comparative viscosity of both solutions (as shown in FIG. 2) at pH 7.4 and 37° C. For the pilocarpine-containing 0.3% Carbopol/14% Pluronic solution, significant lower drug release rates were observed. There was only 1.3% pilocarpine released in the first minute, approximately 76% released after 6 hours, and the release profile was still climbing hereafter. The results indicated that the 0.3% Carbopol/14% Pluronic mixture had better ability to retain drugs than the individual polymer solution and pure STF. The results also suggest that the Carbopol/Pluronic aqueous system can be utilized as an in situ gel-forming system for ophthalmic drug delivery system. Furthermore, by plotting cumulative amount versus square root of time curves for the various formulations (up to 60% of total drug released), linear relationships with correlation coefficients higher than 0.99 can be obtained. The linear relationships in conjunction with the slow dissolution rates suggest that the in vitro drug release from those polymer vehicles at physiological condition occurred primarily by diffusion.

EXAMPLE 4

In vivo Studies

Experimental Design

New Zealand albino rabbits were used as the model animals in the in vivo experiments. Rabbits of either sex, free of gross ocular defects and weighing 2.5–3 kg, were positioned into restraining boxes and placed in an isolated room with 50 W of controlled lighting. The pupillary diameters, which were used to evaluate the pharmacological response of pilocarpine, were measured using a micrometer held at fixed distance from each rabbit. All rabbits were acclimated to laboratory testing conditions for 30 minutes prior to initiate the study. After the 30 minutes period, the left pupil and right pupil diameters were alternatively measured four times within 30 minutes to establish baseline values for both eyes. For each pair of readings, the differences in pupil diameter (control minus test eye) were determined. These predosing difference were averaged and the mean was used to convert post-administration data to the baseline-corrected values. This process minimized both animal and day variation.

Fifty microliters of polymer solutions or simulated tear fluid (STF), each with 1% of pilocarpine hydrochloride, were dosed from a micropipet. Various drug-containing polymer solutions were administered at room temperature and were placed in the lower conjunctival sac, approximately midway between the inner and outer canthus. In order to avoid experimental bias, the left eye of each rabbit was first administered with the control vehicle (formulation with no drug), followed by the application of drug-containing vehicle (formulation with drug), to the right eye. After administration of both the control vehicle and the drug-containing polymer solutions, pupil diameters of both eyes were measured according to the following time schedule: 1, 15, 30, 45, 60, 90, 120, 150, 180, 240, 300, and 360 minutes. For each time point, the difference in pupil diameter (control minus test eye) was calculated; the data were then converted to baseline-corrected value (i.e., the pharmacological response of pilocarpine) by subtracting the average baseline difference in pupil diameter for each experiment on the basis of the readings obtained before dosing. To assess the extent of total pharmacological response of the various formulations, areas under the decrease in pupil diameter (Δ pupil diameter, after baseline correction) versus time profiles in 360 minutes ($AUC_{0-360}$) were calculated using the trapezoidal rule.

Results

Figure 5:
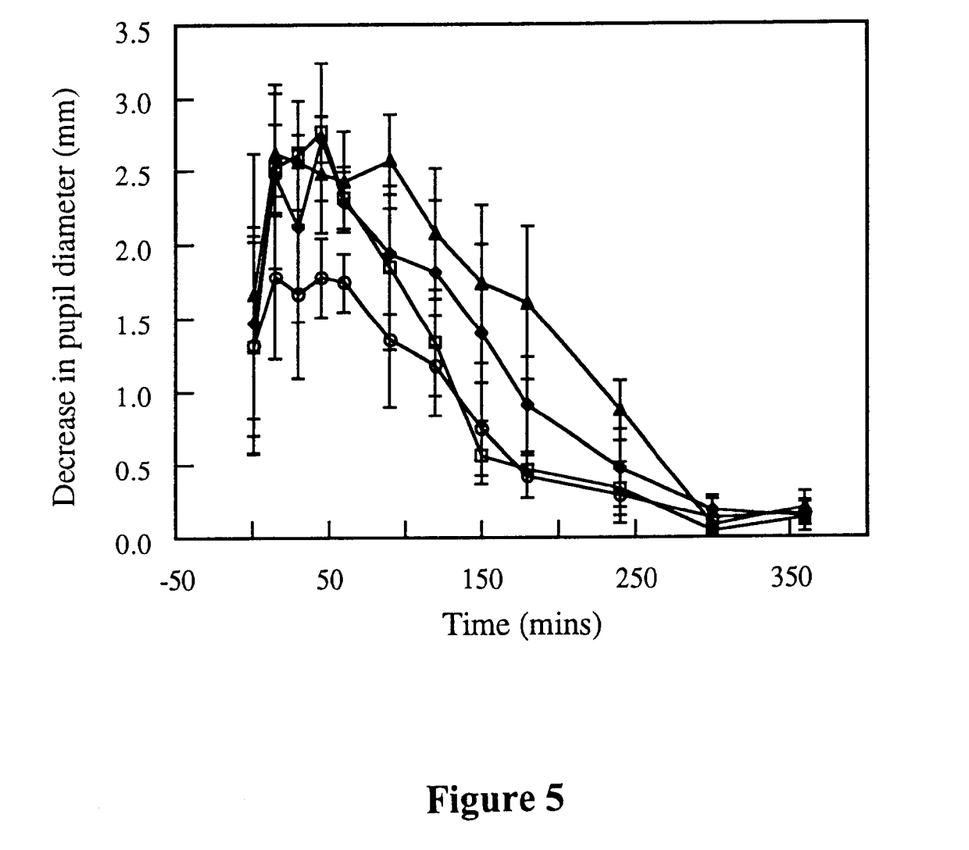
FIG. 5 shows the decrease in pupil diameter versus time profiles for various pilocarpine-containing solutions. (□) shows pilocarpine-containing 0.3% Carbopol solution, (♦) shows pilocarpine-containing 14% Pluronic solution, (▲) shows pilocarpine-containing 0.3% Carbopol/14% Pluronic solution, and (○) shows pilocarpine-containing STF.

FIG. 5 shows the pharmacological response (the decrease in pupil diameter, Δ pupil diameter) versus time profiles for the various pilocarpine-containing polymer solutions and the pilocarpine-containing STF. For the Carbopol/Pluronic formulation, the pharmacological responses were significantly higher than the STF between 5 minutes and 240 minutes of experimental times. A similar phenomenon was also observed for the Pluronic solution. However, the Δ pupil diameters were slightly lower than those of the Carbopol/Pluronic formulation between 90 minutes and 240 minutes of experimental times. As compared to the pilocarpine-containing STF, the Carbopol formulation had higher Δ pupil diameters between 5 minutes and 90 minutes of experimental times and a similar profile can be observed afterwards. These results indicate that the overall miotic responses were greater for the drug-containing polymer formulations than the drug-containing STF. Despite the fast in vitro release rates for pilocarpine in STF (FIG. 4), higher initial in vivo pharmacological responses were not observed. Since several factors affecting the in vivo drug performance, including the blinking of eyes, lacrimal secretion as well as nasolacrimal drainage were not considered in the performing of in vitro dissolution experiment. The in vitro drug release percentage thus may not directly reflect the pharmacological response for those drug-containing vehicles studied.

Table 1 listed the area under the Δ pupil diameter versus time profiles in 360 minutes ($AUC_{0-360}$) for various polymer as well as STF formulations. The results indicate that a 1.85 fold increase in total miotic response was obtained for the Carbopol/Pluronic solution relative to the drug-containing STF. Less pronounced enhancement of total pharmacological response was observed for the other two polymer formulations, i.e., 1.24 and 1.5 times increase in miotic response were obtained for the drug-containing Carbopol and Pluronic solutions, receptively. These in vivo results, along with the rheogram as well as in vitro drug release studies, demonstrate that the Carbopol/Pluronic solution may significantly prolong the drug contact time and thus increase its pharmacological response. Those in vitro and in vivo results all support that the combined Carbopol as well as Pluronic solution can be a promising in situ gelling vehicle for ophthalmic drug delivery.

TABLE 1

The area under the Δ pupil diameters versus time profiles in 360 minutes ($AUC_{0-360}$) for various formulations

| Formulations | $AUC_{0-360}$ | Ratio |
|---|---|---|
| Carbopol | 339.7 (46.4)* | 1.24 |
| Pluronic | 410.2 (92.0)* | 1.50 |
| Carbopol/Pluronic | 507.6 (98.9)* | 1.85 |
| STF | 274.4 (16.4)* | |

*The numbers in parenthesis are standard errors of the mean.

Having described the invention in detail and by reference to the preferred embodiments it will be apparent to those skilled in the art that modifications and variations are possible without departing from the scope of the invention as defined in the following appended claims.

We claim:

1. An ophthalmic drug delivery formulation comprising:

a carboxy vinyl polymer having a molecular weight of about 3,000,000, wherein said carboxy vinyl polymer is about 0.3% by weight; and a polyoxyethylene-polyoxypropylene block copolymer, wherein said polyoxyethylene-polyoxypropylene block copolymer has the chemical structure of $H[OCH_2CH_2]_{49}[OCHCH_2]_{67}[OCH_2CH_2]_{49}OH$ and is about 14% by weight;

whereby said formulation is free flowing at pH 4.0 and 25° C. and forms gel at pH 7.4 and 37° C.

2. The ophthalmic drug delivery formulation according to claim 1, further comprising an ophthalmic drug.

3. The ophthalmic drug delivery formulation according to claim 2, wherein said ophthalmic drug is pilocarpine hydrochloride.

4. A method for preparing the ophthalmic drug delivery formulation comprising:

dispersing a carboxyl vinyl polymer having a molecular weight of about 3,000,000 in water to form a carboxy vinyl polymer solution; and dispersing a polyoxyethylene-polyoxypropylene block copolymer having the chemical structure of $H[OCH_2CH_2]_{49}[OCHCH_2]_{67}[OCH_2CH_2]_{49}OH$ in the carboxy vinyl polymer solution to form an ophthalmic drug delivery formulation;

wherein said carboxy vinyl polymer is about 0.3% by weight and said polyoxyethylene-polyoxypropylene block copolymer and is about 14% by weight of the ophthalmic drug delivery formulation.

5. The method for repairing the ophthalmic drug delivery formulation according to claim 4, further comprising:

dispersing an ophthalmic drug in said ophthalmic drug delivery formulation.

6. The method for preparing the ophthalmic drug delivery formulation according to claim 5, wherein said ophthalmic drug is pilocarpine hydrochloride.

7. A method for treating patients with an eye disease comprising:

topically administering to the patient an effective amount of the ophthalmic drug delivery system according to claim 2.

8. The method for treating patients with an eye disease according to claim 7, wherein said eye disease is glaucoma.

9. The method for treating patients with eye diseases according to claim 8, wherein said ophthalmic drug is pilocarpine hydrochloride.

10. The method for treating patients with eye diseases according to claim 7, wherein said ophthalmic drug delivery system has a pH of no more than 5.5.

11. The ophthalmic drug delivery formulation according to claim 1, wherein said carboxy vinyl polymer is Carbopol 934P.

12. The ophthalmic drug delivery formulation according to claim 1, wherein said polyoxyethylene-polyoxypropylene block copolymer is Pluronic F-127.

13. The ophthalmic drug delivery formulation according to claim 1, wherein said drug delivery formulation has a miotic response which is about 1.85 times better than a drug in a simulated tear fluid (STF) solution.

14. The ophthalmic drug delivery formulation according to claim 1, wherein said drug delivery formulation has a miotic response which is about 1.24 times better than a drug in a simulated tear fluid (STF) solution.

15. The ophthalmic drug delivery formulation according to claim 1, wherein said drug delivery formulation has a miotic response which is about 1.5 times better than a drug in a simulated tear fluid (STF) solution.

* * * * *